US007272205B2

(12) United States Patent
Thibault et al.

(10) Patent No.: US 7,272,205 B2
(45) Date of Patent: Sep. 18, 2007

(54) METHODS, APPARATUS, AND SOFTWARE TO FACILITATE COMPUTING THE ELEMENTS OF A FORWARD PROJECTION MATRIX

(75) Inventors: Jean-Baptiste Thibault, Milwaukee, WI (US); Ken David Sauer, South Bend, IN (US); Charles Addison Bouman, West Lafayette, IN (US); Jiang Hsieh, Brookfield, WI (US)

(73) Assignees: Purdue Research Foundation, West Lafayette, IN (US); General Electric Company, Schenectady, NY (US); The University of Notre Dame Du Lac, Notre Dame, IN (US)

( * ) Notice: Subject to any disclaimer, the term of this patent is extended or adjusted under 35 U.S.C. 154(b) by 104 days.

(21) Appl. No.: 10/990,795

(22) Filed: Nov. 17, 2004

(65) Prior Publication Data

US 2006/0104408 A1   May 18, 2006

(51) Int. Cl.
*G01N 23/083* (2006.01)
(52) U.S. Cl. .......................................... 378/4; 378/901

(58) Field of Classification Search ................. 378/4, 378/15, 901
See application file for complete search history.

(56) References Cited

U.S. PATENT DOCUMENTS

| | | | | |
|---|---|---|---|---|
| 5,218,534 A | * | 6/1993 | Trousset et al. | 382/132 |
| 5,963,612 A | * | 10/1999 | Navab | 378/4 |
| 6,271,862 B1 | * | 8/2001 | Yu | 345/620 |
| 6,459,754 B1 | * | 10/2002 | Besson et al. | 378/4 |
| 6,754,299 B2 | * | 6/2004 | Patch | 378/15 |
| 6,907,102 B1 | * | 6/2005 | Sauer et al. | 378/19 |
| 2007/0003132 A1 | * | 1/2007 | Proksa et al. | 382/154 |

OTHER PUBLICATIONS

Gengsheng L. Zeng et al., "Iterative Reconstruction with Attenuation Compensation from Cone-Beam Projections Acquired via Nonplanar Orbits", IEEE Transactions on Nuclear Science 44(1), 98-106 (1997).*

* cited by examiner

*Primary Examiner*—Allen C. Ho
(74) *Attorney, Agent, or Firm*—Armstrong Teasdale LLP (57) ABSTRACT

A method for calculating an element of a projection includes calculating an element $A_{i,j}$ of a projection matrix using at least two different rays through a voxel.

23 Claims, 4 Drawing Sheets

METHODS, APPARATUS, AND SOFTWARE TO FACILITATE COMPUTING THE ELEMENTS OF A FORWARD PROJECTION MATRIX

BACKGROUND OF THE INVENTION

This invention relates generally to methods, apparatus, and software for iterative image reconstruction and, more particularly, to accurate geometric forward modeling.

In Computed Tomography (CT) diagnostic imaging, the evolution of the scanning geometry into three-dimensional space as the detector size increases and the scanning trajectory evolves is creating a new category of issues for image reconstruction algorithms. In particular, the increasing number of slices on the detector creates significant deviation from the conventional two-dimensional representation of conventional reconstruction techniques, such as Filtered Back-Projection (FBP). Accounting for the conic nature of the x-ray beam becomes desirable to eliminate image artifacts. Among other techniques that are currently being studied to address the issue, Iterative Reconstruction (IR) is a candidate with excellent promise. It allows inclusion of the exact geometry of the scanning trajectory though accurate modeling.

Iterative Reconstruction relies on successive operations of forward and backprojection to obtain the convergence of a derived optimization criterion, which is a measure of the difference between the true measurements and the forward projection of the estimated reconstructions. Let x be the discrete vector of three-dimensional reconstructed space. x's elements represent the unknown densities of the elements of space forming the 3-D volume and are the object of the reconstruction. In addition, let y be the discrete vector of measurements along a number of projection directions. y's elements represent the line integrals through the imaged object for a variety of positions and projection angles that follow the acquisition trajectory and let F(x) be the expected values of the sinogram when the 3-D cross section being reconstructed is assumed to be x. Importantly, the model F(x) includes the precise geometry of the scan pattern and the source/detector structure, so it can directly account for the scan measurements. The difference between the measurements y and their expected values is commonly referred to as "noise," and may be incorporated into the model in the equation y=F(x)+n, where n represents the noise vector. Then, the reconstruction problem may be transformed into the following optimization problem $$\hat{x} = \underset{x}{\operatorname{argmin}} \left\{ \sum_{i=0}^{M} D_i(y_i, F_i(x)) + U(x) \right\} \quad (1)$$

where the functional $D_i$ penalizes the distance between measurement i and the corresponding simulated i-th forward projection of x, U is a scalar valued regularization term which penalizes local differences between voxel elements, and F is a transformation of the image space x in a manner similar to the CT scanning system. A common embodiment of (1) takes the form $$\hat{x} = \underset{x}{\operatorname{argmin}} \left\{ \sum_{i=0}^{M} w_i |y_i - F_i(x)|^2 + U(x) \right\} \quad (2)$$

where $w_i$ is a constant which weights the contribution of measurement i to the objective function. Frequently, a linear model of the form F(x)=Ax is used, linearizing the relation between x and y with a matrix A.

The iterative reconstruction (IR) algorithm works by finding perturbations of the image space x that help to minimize the quantity in (1) or (2), which is a measure of the discrepancy between the actual measurements y and the estimated forward projection F(x) of the image space. It would be desirable to provide improvements to the known IR algorithms.

BRIEF DESCRIPTION OF THE INVENTION

In one aspect a method for calculating the contribution from a voxel element to the acquired data is provided. The method includes calculating an element $A_{i,j}$ of a projection matrix relating voxel j to detector cell i using at least two different rays through a voxel.

In another aspect, a Computed Tomography (CT) System is provided. The system includes a radiation source, a radiation detector, and a computer coupled to the radiation source and the radiation detector. The computer is configured to calculate an element $A_{i,j}$ of a projection matrix relating voxel j to detector cell i using at least two different rays through a voxel.

In yet another aspect, a computer readable medium encoded with a program is provided. The program is configured to instruct a computer to calculate an element $A_{i,j}$ of a projection matrix relating voxel j to detector cell i using at least two different rays through a voxel.

DETAILED DESCRIPTION OF THE INVENTION

Figure 3:
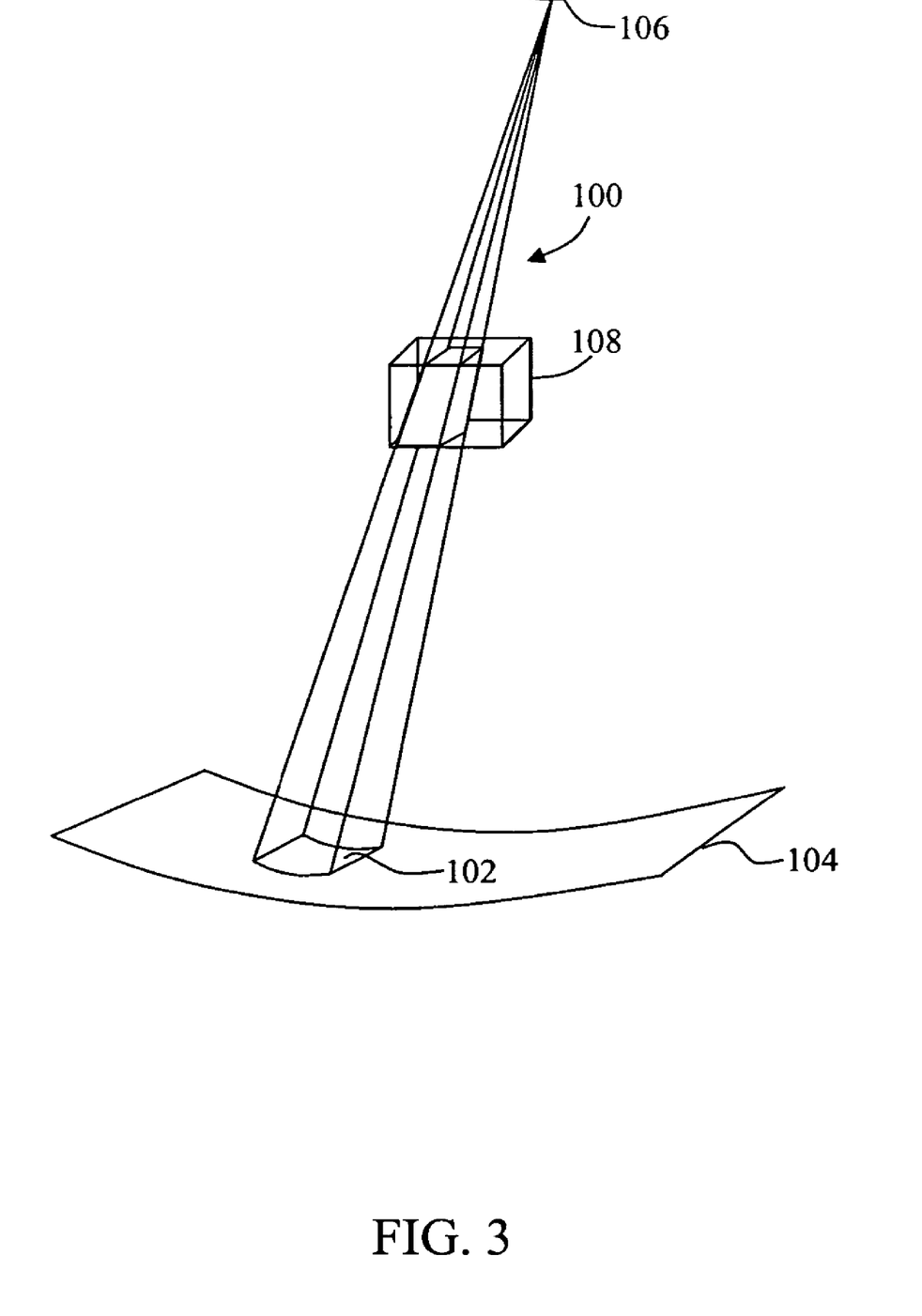
FIG. 3 illustrates a three-dimensional intersection between a three-dimensional voxel, and a cone-shaped x-ray beam that is subtended on one end by the surface of a detector element on a detector plane, and on the other end by the surface and shape of the source at a radiation source.

Each entry of the matrix A represents the model of the effect of a single element of three-dimensional space on the attenuation measurements in the acquired projection data. Note that the reconstructed voxel values in x are linear attenuation coefficients with units of inverse distances. In order to make the product Ax dimensionless, the coefficients of the matrix A have units of length. In a typical reconstruction, a given entry of A is used twice per iteration for both operations of forward and back-projection. The sparsity of the operator A is very large because each possible ray between the source and the detector intersects only a small fraction of the total voxels. The accurate calculation of those non-zero entries is at the heart of the iterative reconstruction problem. It drives complexity, image quality, and performance. The level of accuracy of the calculation greatly contributes to the level of artifacts in the reconstructed image and therefore demands that complex models are used. Considering each detector element paired with image space elements as points typically generates a level of artifacts prohibitive to the acceptance of iterative reconstruction algorithms in a clinical environment. Therefore, each element of space should be considered as solids in three dimensions, or voxels, while each element of the detector should be viewed as a two dimensional surface. The more accurate geometric model of the operator A therefore relies on the average ray intersection length with the voxel, averaged over the surface of the detector cell. For a fixed detector size, this is equivalent to calculating the volumetric intersection between the cone-shaped x-ray beam originating at a radiation source and subtended by the surface of an element of the detector, and a three-dimensional voxel of space, and scaling this coefficient into units of length. FIG. 3 illustrates an example of such volumetric intersection between the 3-D x-ray beam and a rectangular voxel. In one embodiment, the coefficient $A_{i,j}$ of A may be calculated from the average of the intersection lengths of a number of rays cast from the source into the surface of detector element i, with a three dimensional voxel j.

In some known CT imaging system configurations, a radiation source projects a fan-shaped beam which is collimated to lie within an X–Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to reconstruct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm. Thus, methods and apparatus are described herein that have a technical effect of producing a volumetric CT three-dimensional (3D) image of a scanned object.

Three-dimensional (3D) or cone beam (CB) filtered backprojection (FBP) is used in multi-row CT scanners to provide volumetric CT (VCT) scanning operation. Methods are well known to use 3D backprojection algorithms in VCT scanners to reconstruct images using a mapping process. For example, 3D FBP may be used for image reconstruction from cone beam projections acquired from a circular source trajectory. Using a pixel based backprojection, a mapping process is typically performed from the center of a reconstructed pixel to a detector plane.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Figure 1:
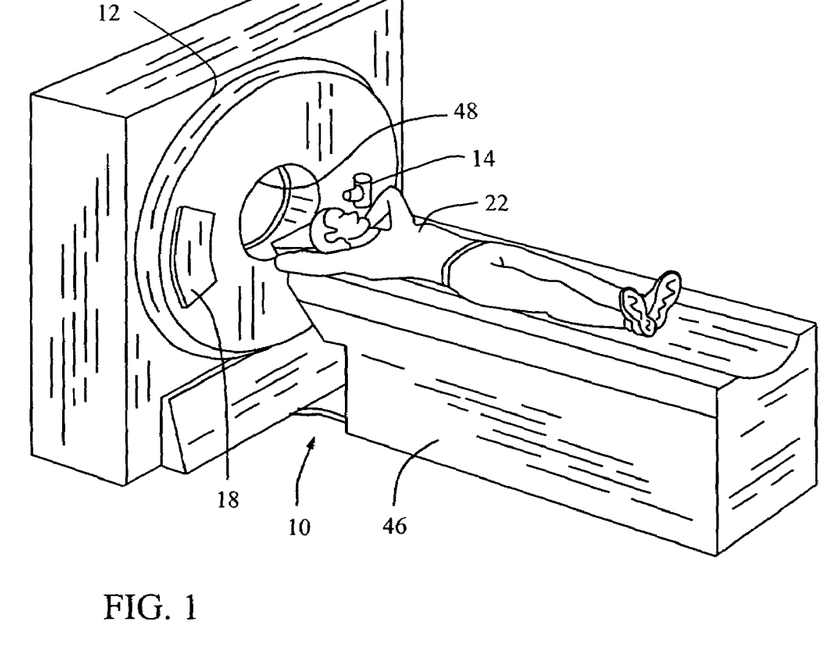
FIG. 1 is a pictorial view of a CT imaging system embodiment.
Figure 2:
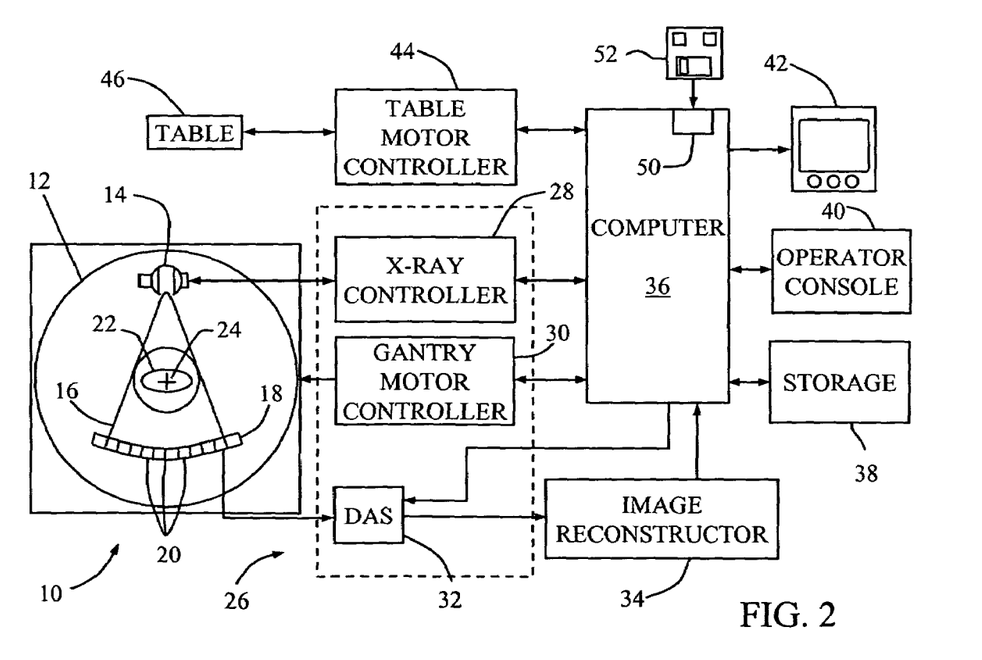
FIG. 2 is a block schematic diagram of the system illustrated in FIG. 1.

FIG. 1 is a pictorial view of a multi slice volumetric CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system. Gantry 12 has a radiation source 14 that projects a cone beam 16 of X-rays toward a detector array 18 on the opposite side of gantry 12.

Detector array 18 is formed by a plurality of detector rows (not shown) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, radiation controller 28, and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Generally, a processor in at least one of DAS 32, reconstructor 34, and computer 36 shown in FIG. 2 is programmed to execute the processes described below. Of course, the method is not limited to practice in CT system 10 and can be utilized in connection with many other types and variations of imaging systems. In one embodiment, Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

Herein described are new methods, apparatus, and software for accurate geometric forward modeling of third generation CT scanners that is suitable for iterative reconstruction of high quality clinical images for medical diagnostic purposes. The herein described methods support all configurations of CT scanners, including single-slice and multi-slice CT, as well as any trajectory of acquisition, such as step-and-shoot (axial) mode, helical mode, or any other mode, with constant or varying pitch and sampling patterns. The herein described methods are also applicable to fourth and fifth generation scanners such as a electron beam CT scanner (EBCT) such as are commercially available from GE Imatron of South San Francisco, Calif.

The forward modeling of the CT scanner in iterative reconstruction requires the accurate computation of volumetric intersections between the x-ray beam and image space voxels. FIG. 3 illustrates a three-dimensional cone-shaped x-ray beam 100 that is subtended on one end by a surface of a detector element 102 on a detector plane 104, and on the other end by the surface and shape of a focal spot at a radiation source 106. A cube voxel 108 is illustrated in FIG. 3 but any particular voxel shape, form, and size may be considered. For example, voxels may be cubes, or rectangular solids in three dimensions, with all voxels packing to cover the full reconstruction space. Alternatively, voxels may be spheres, ellipsoids, cylinders, or spherically symmetric elements of space, with set properties of overlap and coverage of the reconstruction space. In addition, voxels may have fuzzy boundaries determined after statistical properties of the reconstruction space so as to minimize reconstruction artifacts. The voxel size controls the resolution of the reconstructed images. In general, the voxel size can be a function of the images produced by another reconstruction method and used as initial conditions for the iterative reconstruction. Alternatively, the voxel size can be a function of the size of the detector elements, of the pitch of the acquisition (i.e. the distance traveled by the CT table for each rotation of the gantry), or more generally of the sampling pattern used during data acquisition.

Since no closed-form formulation exists for the volumetric intersection between the x-ray beam and the voxels, one has to rely on approximations. Typically, the first approximation consists of considering the x-ray beam as a single line between the center of the focal spot and the center of the detector element, and to calculate the line intersection with a voxel element. The entries of A at row i and column j then become the length of the line segment between the source and detector i lying within voxel j. For cubic or rectangular shaped voxels, such intersection with the line segment can be computed exactly with line-clipping algorithms such as Cyrus-Beck or other algorithms, and their extensions into three dimensions. Because of the very large number of projections necessary to describe a real system, which typically includes about 1000 projections per rotation for more than 16 detector rows, and about 1000 channels per row, it is desirable to use clipping algorithms that quickly eliminate rays that do not cross the voxel considered. For instance, the Liang-Barsky line-clipping algorithm and its extension into three dimensions allows to quickly identify the cases that do not yield an intersection by aligning the vertices of the voxels along the three axis of the CT system. The numerical values of the intersections for a variety of lines crossing the voxels may be calculated inline during the reconstruction for any ray, or pre-calculated offline for a number of rays and stored into lookup tables for fast and easy access during the reconstruction. In the embodiment using a lookup table, the length of the intersection for a particular ray-voxel pair can be calculated by interpolation as a function of the parameters indexing the lookup tables.

Figure 4:
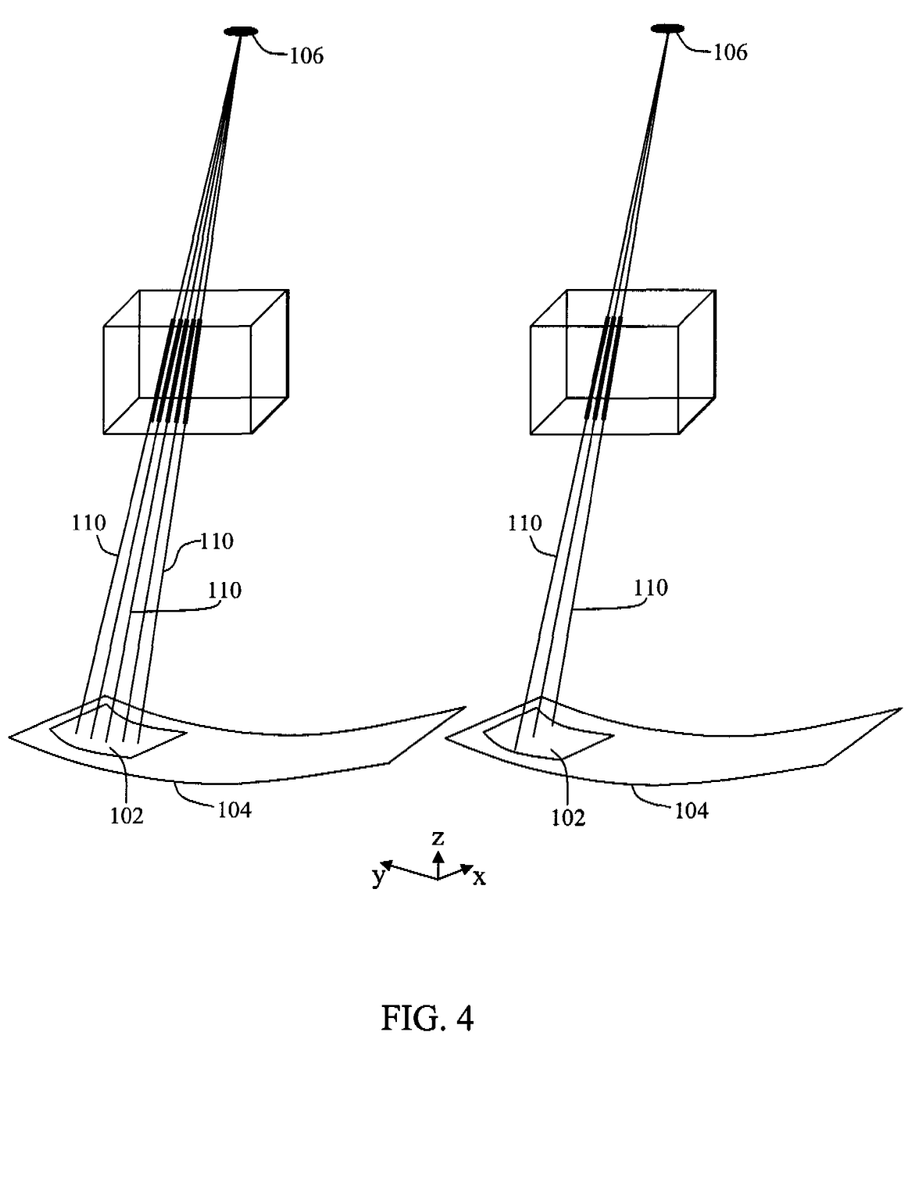
FIG. 4 illustrates an example of multiple rays cast between one point at a source and multiple points on a detector, as a possible sampling pattern to calculate an element $A_{i,j}$ of a projection matrix.

However, using the length of a single line segment as an estimate of the contribution of a voxel element to the measured radiation at a detector element is but a coarse approximation to the true volumetric intersection between the x-ray beam and the voxel. Therefore, instead of using a single projection from the source to the detector to calculate the intersection, one embodiment relies on multiple projections for each voxel and source-detector pair. For each source position and detector cell pair i, consider a number of projection rays from the source to the detector. The coefficients $A_{ij}$ of the projection matrix for voxel j can be calculated as the average length of intersection between all projection rays for the source-detector pair i and the voxel. It is proportional to the volume of intersection between the voxel and the X ray beam. Using coefficients calculated from multiple rays results in greatly improved image quality over coefficients calculated from a single ray. Computing each element $A_{ij}$ using multiple rays is equivalent to calculating a numerical integration over the volume of the intersection of the x-ray beam with the voxel. The accuracy of the numerical integration over the volume of the intersection can be made as high as desired by increasing the density of the points where the projections fall within the element of detector. This concept of considering multiple rays is referred to as "upsampling". FIG. 4 illustrates the process of upsampling in two dimensions on detector element 102 of detector plane 104. For each voxel and source-detector pair, a number of points are considered within the surface of the detector element, and rays are cast between each point and the source. The intersection length of each ray with the voxel is calculated separately, and then a weighted sum calculated whose coefficients are based on the chosen upsampling pattern.

In the example of FIG. 4, multiple rays 110 are cast between one point at source 106 and multiple points on detector element 102. Similarly, multiple rays can be cast between one point at detector element 102 and multiple points within the focal spot at source 106. Thus the forward model can account for the size, shape, motion, and distribution, or other properties, of the focal spot and the x-ray source in general. Multiplying the number of projections permits more accurate measurement of the contribution of a voxel of the object to the radiation measured by one element of the detector for a given source position. Upsampling can be on the detector, at the source, or both.

In FIG. 4, the process is illustrated for upsampling separately along the two dimensions x and y of detector element 102. Similarly, any number of points or any position of those points within each detector element can be selected. The greater the number of points is, the greater the accuracy of the approximation to the true average intersection length. The upsampling factors can be different in all directions. For instance, on the detector, the upsampling factors may be different along the two dimensions of the detector element, or at the source, the positions of the rays cast may be a function of the distance to the center of the focal spot and the distribution of the x-ray intensity. The resulting sampling pattern can be uniform, or have varying density, or be adaptively selected based on the location, shape, and/or other general geometry and physical properties of the detector element.

The upsampling can also be designed to accurately model the relationship between the entire physics of the CT scanning system and the reconstruction space. In general, the upsampling pattern can be adaptively selected based on the intensity, shape, texture, and/or other properties of the imaged object. Upsampling can also be adaptively selected depending on the spatial position of the voxel relative to the detector element, and/or depending on the size of the voxel element, and/or the size of the image elements relative to the size of the detector elements.

The upsampling can also be used to describe accurately the geometry and physical properties of the detection system. The detector channels dimensions and dead space between detector channels can be taken into account by limiting the upsampling pattern for any detector channel to the actual area of the single detector channel that effectively received x-ray photons. By ensuring that substantially no rays can fall within the dead space between the detector channels, the forward model including the detector non-idealities is more precise.

Thus, the computation of the forward model for the CT scanning system uses a number of projections for each voxel and source-detector pair. The projection method is not limited to single rays. Each projection ray can be a single pencil beam with a one-dimensional intersection with the voxel (calculating the length of the intersection as described with respect to FIG. 4), or any other shape, such as 2-D planes (calculating the surface of the planar intersections with the voxel), or cylinders, parallelepiped, etc., and/or a collection of all of the above.

For each voxel and source-detector pair, upsampling relies on a collection of single intersection measurements before taking their weighted sum over the number of projections. The coefficients of the weighted sum may be selected based on the upsampling pattern. Also, the measurement for each projection may be calculated completely separately. These may rely on the same exact intersection method for each. However, gains in computation time may result if the calculation for some projections can be a function of one or more other projections. For instance, the first projection intersecting the voxel may be calculated exactly, and intersections for other rays approximated based on the exact intersection as a function of the difference between the parameters describing each ray and the voxel shape and size. Other algorithms for computing intersections such as these developed for computer graphics may be applied to this context of forward projection for iterative reconstruction for CT.

To speed up computation time, the intersections of a number of projections through a voxel can be computed offline and stored in memory in a lookup table. Then for any voxel and source-detector pair, the intersection can be calculated as the interpolation between stored values, scaled by a function of the distance between the voxel and the detector. Computations can also be sped up through the use of special purpose hardware, FPGAs, ASICs, special purpose graphics hardware, or massive parallel computer clusters, in order to compute simultaneously the intersections for a very large number of projections and a large number of voxels through parallel implementation.

In the description of this iterative approach to image reconstruction, the system matrix A has thus far been treated as a stationary process. That is to say, it is fully a function of the geometry of the system, and does not change over time. However, the system matrix may be adjusted during reconstruction to address temporal effects such as patient motion. This is particularly relevant for cardiac imaging, for instance. That is, the system matrix generation may dynamically change with the motion map over the process of reconstruction. If one associates each voxel with a specific location in patient anatomy, the location of the voxel may be described by a four dimensional variable (x, y, z, t) of the three spatial coordinates and time. The generation of the system matrix may take into account this four dimensional functional in order to adjust the matrix coefficients over time, as an embodiment to address motion correction.

Figure 5:
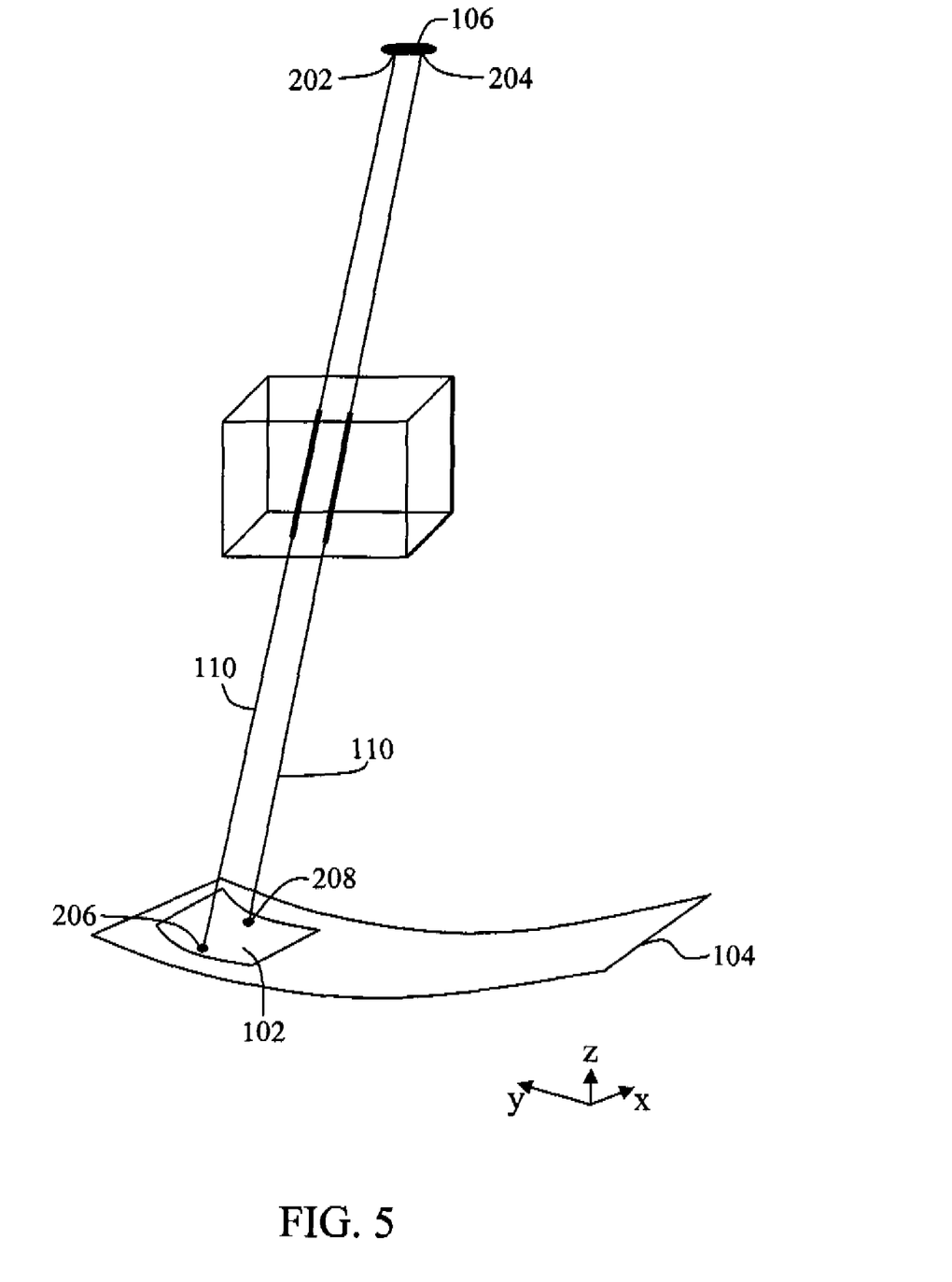
FIG. 5 illustrates an example of rays cast between multiple points at a source and multiple points on a detector.

FIG. 5 illustrates an example of multiple rays cast between a plurality of points of a source and multiple points of a detector. Ray 110 is cast from a point 202 of source 106 via a voxel towards a point 206 on detector element 102 of detector plane 104 and ray 110 is cast from a point 204 of source 106 towards a point 208 on detector element 102. Point 202 is different than point 204 and point 206 is different than point 208. An element $A_{ij}$ of a projection matrix is calculated using rays 110 passing through a voxel.

One technical effect of the herein described methods, apparatus, and software which accrue the advantage of multiple projections is increased accuracy over measurement from single projections, which typically creates artifacts in reconstructed images as a function of resolution and sampling characteristics. Such accuracy is desirable to making images suited to clinical diagnostic with iterative reconstruction, which provides other benefits in terms of noise, resolution, artifacts reduction, etc., over conventional methods. The herein described methods, apparatus, and software provide accurate forward projection in any geometry for use in iterative reconstruction, which is another technical effect. This is applicable to all generations of CT scanners.

While the invention has been described in terms of various specific embodiments, those skilled in the art will recognize that the invention can be practiced with modification within the spirit and scope of the claims.

What is claimed is:

1. A method for calculating an element of a projection matrix, said method comprising:
    dividing an object into a plurality of voxels;
    generating an X-ray beam from a source;
    applying a line-clipping algorithm to the X-ray beam such that a first set of at least two theoretical X-ray lines intersect one of the voxels;
    calculating, during iterative reconstruction, an element $A_{ij}$ of a projection matrix by using the first set of at least two theoretical X-ray lines so that the at least two X-ray lines project through the one of the voxels; and
    storing the calculated element $A_{ij}$ in a computer readable medium to facilitate calculating a volumetric intersection of the one of the voxels.

2. A method in accordance with claim 1, wherein said calculating comprises calculating the element $A_{ij}$ of the projection matrix using the at least two X-ray lines that project through the one of the voxels, wherein the X-ray lines project to a single detector point disposed on a detector.

3. A method in accordance with claim 2, wherein said calculating comprises calculating the element $A_{ij}$ of the projection matrix using the at least two X-ray lines that project through the one of the voxels to the single detector point from a plurality of source points in the source, wherein a distance between the source points in the source is a function of a distance the source points are from a center of the source.

4. A method in accordance with claim 2, wherein said calculating comprises calculating the element $A_{ij}$ of projection matrix using the at least two X-ray lines that project through the one of the voxels to the single detector point from a plurality of source points in the source, wherein a distance between the source points in the source is a function of a distance the source points are from a center of the source and a distribution of x-ray intensity of the source.

5. A method in accordance with claim 1, wherein said calculating comprises calculating the element $A_{ij}$ of the projection matrix using the at least two X-ray lines, wherein the X-ray lines project through the one of the voxels from a single source point.

6. A method in accordance with claim 5, wherein said calculating comprises calculating the element $A_{ij}$ of the projection matrix using the at least two X-ray lines that project through the one of the voxels from the single source point of the source to a plurality of detector points disposed on a detector, wherein a distance between the detector points is a function of a distance one of the detector points is from a center of an element of the detector.

7. A method in accordance with claim 5, wherein said calculating comprises calculating the element $A_{ij}$ of the projection matrix using the at least two X-ray lines that project through the one of the voxels from the single source point to a plurality of detector points disposed on a detector, wherein a distance between the detector points is a function of a distance one of the detector points is from a center of an element of the detector and a distribution of sensitivity of the element of the detector.

8. A method in accordance with claim 1, wherein said calculating comprises calculating the element $A_{ij}$ of the projection matrix using the at least two X-ray lines that project through the one of the voxels, wherein an upsampling in a first direction is different from an upsampling in a second direction.

9. A method in accordance with claim 8 wherein the first and second directions are orthogonal.

10. A method in accordance with claim 1, wherein said calculating comprises calculating the element $A_{ij}$ of the projection matrix using the at least two X-ray lines, wherein the X-ray lines are adaptively selected based on at least one of a detector element location, a detector element shape, a detector geometry, and a physical detector property of a detector that detects the X-ray lines.

11. A method in accordance with claim 1, wherein said calculating comprises calculating the element $A_{ij}$ of the projection matrix using the at least two X-ray lines, wherein the X-ray lines are adaptively selected based on at least one of an object intensity, an object shape, an object texture, and an object property.

12. A method in accordance with claim 1, wherein said calculating comprises calculating the element $A_{ij}$ of the projection matrix using the at least two X-ray lines, wherein the X-ray lines are adaptively selected based on at least one of a spatial position of the one of the voxels relative a detector element, a size of the one of the voxels, and a ratio of an image element size to a detector element size.

13. A method in accordance with claim 1, wherein said calculating comprises calculating the element $A_{ij}$ of the projection matrix using the at least two X-ray lines selected such that the at least two of the X-ray lines do not terminate in a dead space between detector channels.

14. A method in accordance with claim 1, wherein said calculating comprises calculating the element $A_{ij}$ of the projection matrix using a plurality of the at least two X-ray lines with varying spacing among the at least two of the X-ray lines.

15. A method in accordance with claim 1 further comprising re-calculating the element $A_{ij}$ of the projection matrix using a second set of the at least two X-ray lines that project through the one of the voxels at a time subsequent to the first calculation of the element $A_{ij}$ to at least partially compensate for motion.

16. A method in accordance with claim 1, wherein said calculating comprises calculating the element $A_{ij}$ of the projection matrix using the at least two X-ray lines that project through the one of the voxels, said at least two X-ray lines comprising a first X-ray line comprising a first start point and a first end point and a second X-ray line comprising a second start point and a second end point, wherein said first start point is different from said second start point, and said first end point is different from said second end point.

17. A Computed Tomography (CT) System comprising:
    a radiation source;
    a radiation detector; and
    a computer coupled to said radiation source and said radiation detector, said computer configured to:
    divide an object into a plurality of voxels;
    generate an X-ray beam from the radiation source;
    apply a line-clipping algorithm to the X-ray beam such that a first set of at least two theoretical X-ray lines intersect one of the voxels;

calculate, during iterative reconstruction, an element $A_{ij}$ of a projection matrix by using the first set of at least two theoretical X-ray lines so that the at least two X-ray lines project through the one of the voxels; and store the calculated element $A_{ij}$ in a computer readable medium to facilitate calculating a volumetric intersection of the one of the voxels.

18. A system in accordance with claim 17 wherein said computer is further configured to calculate the element $A_{ij}$ by using the at least two X-ray lines that project through the one of the voxels by using a first weight on a first one of the at least two X-ray lines to generate a first weighted X-ray, by using a second weight on a second of the at least two X-ray lines to generate a second weighted X-ray, and summing the first and second weighted X-rays, wherein an intersection of the first of the at least two X-ray lines with the at least one of the voxels is calculated exactly, and an intersection of the second one of the at least two X-ray lines with the at least one of the voxels is approximated.

19. A system in accordance with claim 18 wherein said computer is further configured to calculate the element $A_{ij}$ using the at least two X-ray lines that project through the one of the voxels by using a first weight on a first one of the at least two X-ray lines to generate a first weighted X-ray, by using a second weight on a second of the at least two X-ray lines to generate a second weighted X-ray, and summing the first and second weighted X-rays, wherein the first and second weights are a function of a distance, a voxel size, and a voxel shape.

20. A system in accordance with claim 19 wherein said computer is further configured to calculate the element $A_{ij}$ using the at least two X-ray lines that project through the one of the voxels by using a first weight on a first one of the at least two X-ray lines to generate a first weighted X-ray, by using a second weight on a second of the at least two X-ray lines to generate a second weighted X-ray, and summing the first and second weighted X-rays, wherein the first and second weights are a function of a distance of the one of the voxels to a center of the source.

21. A computer readable medium encoded with a program configured to instruct a computer to:

divide an object into a plurality of voxels;

generate an X-ray beam from a source;

apply a line-clipping algorithm to the X-ray beam such that a first set of at least two theoretical X-ray lines intersect one of the voxels;

calculate, during iterative reconstruction, an element $A_{ij}$ of a projection matrix by using the first set of at least two theoretical X-ray lines so that the at least two X-ray lines project through the one of the voxels; and store the calculated element $A_{ij}$ in the computer readable medium to facilitate calculating a volumetric intersection of the one of the voxels.

22. A computer readable medium in accordance with claim 21 wherein said program is further configured to instruct the computer to calculate the element $A_{ij}$ using the at least two X-ray lines that project through the one of the voxels by using a first weight on a first one of the at least two X-ray lines to generate a first weighted X-ray, by using a second weight on a second of the at least two X-ray lines to generate a second weighted X-ray, and summing the first and second weighted X-rays, wherein the first and second weights are a function of at least one of:

a distance;

a voxel size;

a voxel shape;

a location of a starting point of one of the at least two X-ray lines;

a location of an ending point of one of the at least two X-ray lines;

a motion of the source;

an x-ray intensity; and a scanned object.

23. A computer readable medium in accordance with claim 21 wherein said program is further configured to instruct the computer to re-calculate the element $A_{ij}$ of the projection matrix using a second set of at least two X-ray lines that project through the one of the voxels at a time subsequent to the first calculation of the element $A_{ij}$ to at least partially compensate for motion.

* * * * *